United States Patent [19]

Kritzinger et al.

[11] Patent Number: 5,934,285
[45] Date of Patent: Aug. 10, 1999

[54] METHOD FOR REDUCING IRREGULAR ASTIGMATISM AND DEBRIS/EPITHELIUM IN THE INTERFACE DURING LAMELLAR CORNEAL FLAP/CAP SURGERY

[75] Inventors: Michiel S. Kritzinger, 26 Wexford Avenue, Westcliff, Johannesburg, South Africa; Stephen A. Updegraff, Rapid City, S. Dak.

[73] Assignee: Michiel S. Kritzinger, South Africa

[21] Appl. No.: 08/562,253

[22] Filed: Nov. 22, 1995

Related U.S. Application Data

[60] Provisional application No. 60/001,592, Jul. 27, 1995.

[51] Int. Cl.⁶ .................................................. A61B 19/00
[52] U.S. Cl. .......................... 128/898; 606/161; 606/166
[58] Field of Search ..................... 606/160, 161, 606/166, 167, 107; 128/898; 604/257, 35, 264

[56] References Cited

U.S. PATENT DOCUMENTS

| | | |
|---|---|---|
| 3,818,913 | 6/1974 | Wallach . |
| 4,357,941 | 11/1982 | Golubkov et al. . |
| 4,406,285 | 9/1983 | Villasenor et al. . |
| 4,417,579 | 11/1983 | Soloviev et al. . |
| 4,515,157 | 5/1985 | Fedorov et al. . |
| 4,705,035 | 11/1987 | Givens . |
| 4,739,761 | 4/1988 | Grandon ................................ 606/166 |
| 4,744,360 | 5/1988 | Bath . |
| 4,963,142 | 10/1990 | Loertscher ............................... 606/14 |
| 5,226,905 | 7/1993 | Hanna ..................................... 606/166 |
| 5,250,062 | 10/1993 | Hanna ..................................... 606/166 |
| 5,312,330 | 5/1994 | Klopotek ................................. 604/49 |
| 5,314,439 | 5/1994 | Sungita .................................... 606/166 |
| 5,342,378 | 8/1994 | Giraud et al. .......................... 606/166 |
| 5,407,441 | 4/1995 | Greenbaum .......................... 604/280 |
| 5,458,610 | 10/1995 | Feaster ................................... 606/166 |
| 5,549,622 | 8/1996 | Ingram ................................... 606/166 |
| 5,571,124 | 11/1996 | Zelman .................................. 606/166 |

Primary Examiner—David H. Willse
Assistant Examiner—Kelly O'Hara
Attorney, Agent, or Firm—Wood, Herron & Evans, L.L.P.

[57] ABSTRACT

A method for reducing irregular astigmatism and debris during lamellar surgery of the eye is practiced by preoperatively marking the corneal surface with a pattern or radial and pararadial lines. After making the incision, the incised corneal cap or flap is removed, followed by reshaping of the corneal stroma, irrigating the corneal bed to wash residual debris, and aspirating fluid from the eye. The corneal cap or flap is then repositioned on the cornea by realignment of the pattern of radial and pararadial lines.

30 Claims, 3 Drawing Sheets

METHOD FOR REDUCING IRREGULAR ASTIGMATISM AND DEBRIS/EPITHELIUM IN THE INTERFACE DURING LAMELLAR CORNEAL FLAP/CAP SURGERY

RELATED APPLICATIONS

This application is a continuation of Provisional Application Ser. No. 60/001,592, filed Jul. 27, 1995, now abandoned, which is incorporated herein in its entirety by reference. This application is also related to application Ser. No. 08/561,744, now U.S. Pat. No. 5,755,700, application Ser. No. 08/561,541, now U.S. Pat. No. 5,697,945, and application Ser. No. 08/562,257, now U.S. Pat. No. 5,779,711 filed on even date herewith and entitled "Corneal Irrigation Cannula and Method of Using", "Corneal Surface Marker and Marking Method for Reducing Irregular Astigmatism During Lamellar (LASIK) Corneal Surgery" and "Corneal Flap/Cap Elevator", respectively, which are incorporated herein in their entireties by reference.

BACKGROUND OF THE INVENTION

Lamellar corneal surgery has undergone a steady evolution over the last 50 years. Advancements in the technology, such as automated keratomes and non-freeze, no-suture techniques have markedly improved safety and effectiveness. During the surface ablation craze of the late 80's, Dr. Gholam Peyman, known for his pioneering retina work, realized the utility of preserving all layers of the cornea but taking advantage of the extreme accuracy of the excimer laser. He patented the method for LASIK years ago and studied this technique in his laboratory. He used a YAG laser due to the limited response and acceptance for this technique by the major excimer laser manufacturers. During the years of epikeratoplasty others such as Drs. Lee Nordan and Stephen Slade, as well as Dr. Casimir Swinger, were learning and developing freeze myopic keratomileusis for high myopia. By the late 80's, Dr. Slade was one of a hand full of surgeons still performing this demanding technique. When Dr. Luis Ruiz introduced the automated keratome and the in situ non-freeze, no-suture technique to the lamellar bed, Dr. Slade embraced this and has since introduced this technique to thousands of surgeons worldwide. Although a significant advancement, even Dr. Luis Ruin realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery, most notably Dr. Lucio Buratto of Milan, Italy, and Dr. Ioannis Pallikaris of Greece. The original Buratto technique, however, required cutting a very thick cap and ablating its under surface. Many of these lenticules required suturing, thus required extreme surgical precision and irregular astigmatism rates were quite high. Pallikaris' early work was done on animal models and provided the first histopathology of excimer laser to a lamellar bed. The early Summit excimer laser studies that evaluated the use of lamellar surgery were conducted by Brink, et al.; however, there was a significant loss of best corrected visual acuity and a wide range of outcomes as new surgeons attempted to perform the original suture dependent Burrato technique.

As surgeons began doing lamellar surgery, they became concerned about the potential for inducing irregular astigmatism as well as introducing debris such as epithelial inclusions in the interface. Fortunately, with the introduction of the automated keratome and non-freeze, non-suture techniques, irregular astigmatism rates are reduced. Debris in the interface, however, continues to be a chronic problem. Many surgeons have resorted to never wearing gloves during lamellar surgery just for that reason. Although infections in lamellar surgery are quite low, when you are the patient that has the infection, percentages do not matter. At present, it is unclear whether or not wearing gloves during lamellar surgery is the standard of care. Thus, we need a way to perform lamellar surgery with gloves safely so as not to introduce debris into the interface.

Recently a very famous clinical researcher in excimer laser technology expressed that his job is now to make surface ablation PRK as good or better than LASIK. Preserving all the layers of the cornea provides quicker visual recovery and the predictability is less dependent upon the ablation characteristics of the laser. Thus, LASIK in its infancy already has a head start over any surface ablation technique. Secondly, PRK retreatment is not predictable, LASIK enhancement is possible. The tremendous amounts of research and development required to create the perfect surface ablation could be better spent in perfecting LASIK for all ranges of refractive errors.

There is a growing need to introduce lamellar surgery skills to surgeons new to this arena. Surgeons who have been performing ALK will be prepared to make an easy transition to LASIK. Many of the surgeons making the transition from PRK to LASIK appear totally consumed in what type of ablation to use in the bed, when in reality their primary concerns should be a safe keratectomy and repositioning the cap/flap so that there is the least likely chance for debris in the interface or irregular astigmatism. If that can be reproduced, then enhancement is possible and predictability of the ablation for each surgeon will increase with experience.

Therefore, notwithstanding developments in lamellar surgery to date, techniques and instrumentation are needed to positively impact all lamellar surgeons who have grappled with sight-threatening irregular astigmatism and debris in the interface.

SUMMARY OF THE INVENTION

This invention is directed to a number of improvements in instrumentation and surgical techniques for reducing irregular astigmatism and debris/epithelium in the interface during lamellar corneal surgery. All of the improvements in instrumentation and surgical techniques are incorporated into the method of the present invention.

The lamellar surgical method for repositioning an excised corneal cap or flap of the present invention begins by preoperatively marking the corneal surface with suitable indicia so that adequate reference marks on the corneal surface are made for incision locations and precise centration and reorientation of the cap or flap onto the corneal bed after surgical reshaping of the corneal stroma.

The corneal surface marker utilized in this method comprises a handle suitable for manipulation by hand and a marking surface or device having two concentric rings ensuring centration of the marker and subsequent centration of other instrumentation with the inner ring of the two concentric rings. Marking radials and pararadials extend off of the inner ring and provide adequate reference points for marking indicia on the corneal surface. The radials and pararadials preferably vary in width and extend beyond the concentric rings thereby permitting accurate anatomic repositioning of a free corneal cap or flap while preventing placement of the cap or flap with the epithelial surface down. In other words, the marker and method of using it also prevents the corneal cap/flap from being placed upside down. The inner concentric ring is also provided with a cross-hair to ensure centration of the marker and subsequent centration of other instrumentation.

Furthermore, the inner and outer concentric rings of the marker are circumferentially sized to outline the corneal surface and the optical zone of the corneal surface ensuring accurate centration of the marker for preoperatively marking the corneal surface with suitable indicia. In accordance with these outlines and in its most preferred form, the inner and outer concentric rings of the marker are approximately 5 mm and 10 mm, respectively. Also, the marking radials and pararadials are sufficiently circumferentially spaced around the concentric rings to provide adequate reference points for marking indicia around the area of the corneal surface to be marked. The pararadials include two pararadials extending off the inner concentric ring which are located at the inferior region of the marker. The pararadials are circumferentially spaced 90 degrees apart in this region. They also are of unequal width, one pararadial being at least twice as wide as the other pararadial permitting accurate anatomic repositioning of a free corneal cap or flap while preventing placement of the cap or flap with the epithelial surface down. The radials located between the nasal, temporal and superior regions of the marker are circumferentially spaced apart equally. The radial positioned superiorly or 90 degrees from the nasal and temporal radials is also at least twice as wide as the other radials positioned in these regions.

The method of marking the corneal surface according to the invention comprises placing the corneal surface marker over the area of the cornea to be marked. The above described marker is then employed for preoperatively marking the corneal surface with suitable indicia, such as pharmacologically acceptable dyes, in accordance with the radials and pararadials of the marker thereby permitting accurate, anatomic repositioning of the free cap or flap. The employment of the radials and pararadials, along with their variance in width enable the accurate anatomic repositioning and prevent the wrong side of the corneal surface (epithelial surface) from being placed onto the corneal bed after the corneal stroma has been surgically reshaped.

Next, epithelium and debris are removed from the interface of the corneal bed and cap or flap after corneal reshaping by irrigating the corneal bed with fluid ejected from a low flow cannula. Irrigation by the cannula preferably is from the center of the bed and moves peripherally thereby removing at low flow the epithelium and debris from the interface while gently elevating the cap or flap with the fluid ejected from the cannula.

The corneal irrigation cannula for use in tectonic lamellar keratoplasty comprises a hand manipulatable tube having one inlet end for receiving an irrigating fluid and an outlet end for delivery of fluid. The tube is of sufficient length to allow for entry into the interface of the corneal flap or cap and a corneal bed after surgical dissection of the corneal surface. The tube is preferably angled to facilitate entry into the interface. The cannula has an end having a plurality of irrigating ports for the low flow delivery of suitable fluid therethrough to the corneal bed or other area to be irrigated. One of the ports is situated at the tip of the end for delivery of the fluid directly outward from the end while the other ports are situated superiorly and inferiorly thereby directing fluid upward and downward from the ports.

The method of using the cannula comprises inserting the outlet end of the cannula into the interface of an overlying corneal cap or flap and corneal bed for the delivery of suitable fluid under low flow or velocity through irrigating ports of the cannula thereby irrigating the interface by gently elevating the overlying cap or flap and washing residual debris and epithelium from the corneal bed. Preferably, the delivery flow of the fluid is from the center of the corneal bed and moves peripherally toward the edge of the bed and cap or flap. The removed fluid and debris may then be aspirated from the edge of the interface and the fornices of the eye which collect residual fluid, debris and unwanted tissue. Finally, alignment of the cap or flap is made to its correct anatomical position with a layer of fluid in the interface utilizing the preoperative surface indicia as outlined above.

The method of this invention may also include an elevating instrument for use in atraumatically lifting a corneal flap or cap during corneal lamellar surgery and if repositioning the corneal cap or flap is unsuccessful. The elevating instrument for use in atraumatically lifting a corneal flap or cap during the surgery comprises a handle and an elevator head. The head has a concave leading edge and a convex face vertically extending from the leading edge and a bottom concave surface extending between the toe and heel of the head to atraumatically engage a corneal edge where initial incision has been made by the surgeon to lift the corneal edge and to expose the underlying surface to be surgically altered or reshaped. Preferably, the instrument has a leading arcuate edge which is dull and has rounded corners thereby preventing tear of the corneal edge to be lifted.

These and other advantages of the present invention will become more apparent from the drawing figures and detailed description.

Also illustrated are the nasal, inferior, temporal, and superior regions surrounding the eye over which the surface marker is properly placed prior to marking the corneal surface.

Figure 2A:
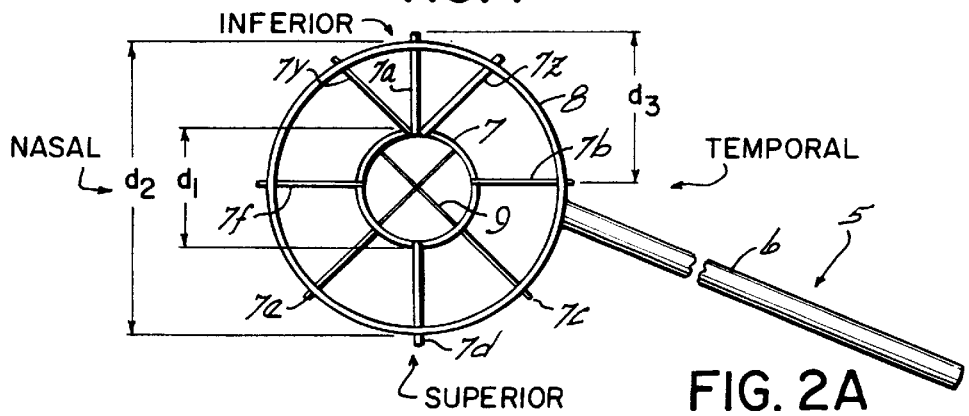
FIG. 2A illustrates a top view of a corneal surface marker for use with the method of the present invention having a handle and two concentric rings having radial blades with dimensional indications.
Figure 2B:
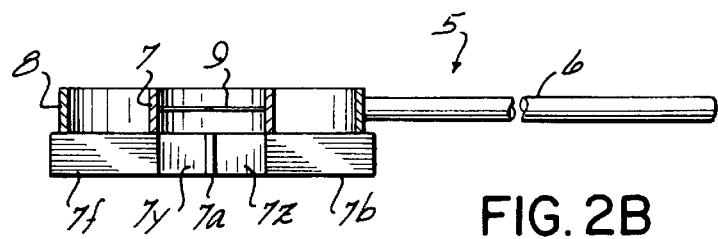

FIG. 2B is a cross-sectional side view of FIG. 2A.

Figures 3A, 3B:
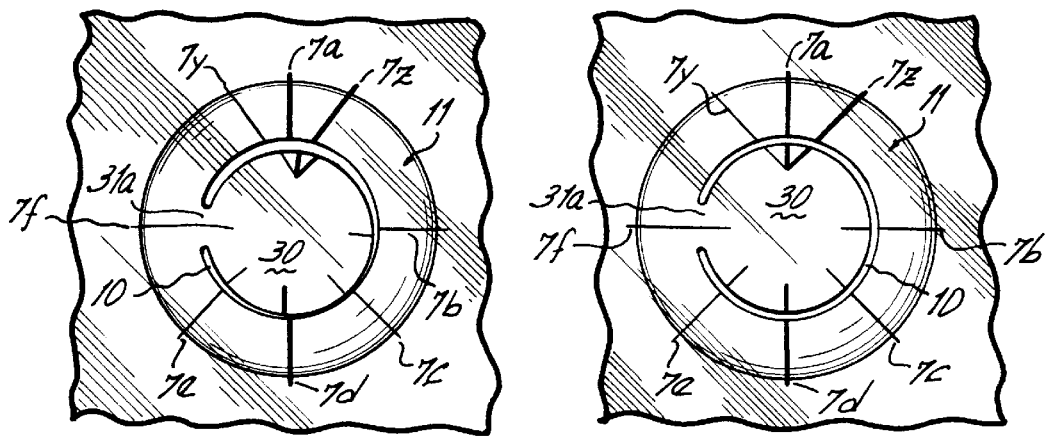

FIG. 3A is an illustration of a misaligned corneal cap post surgical procedure whereby the radial and pararadial marks directed by the corneal surface marker indicate the incorrect positioning of the corneal cap.

FIG. 3B is an illustration of a correctly aligned corneal cap post surgical procedure whereby the radial and pararadial marks directed by the corneal surface marker indicate the correct, accurate and precise anatomical repositioning of the corneal cap.

Figure 4:
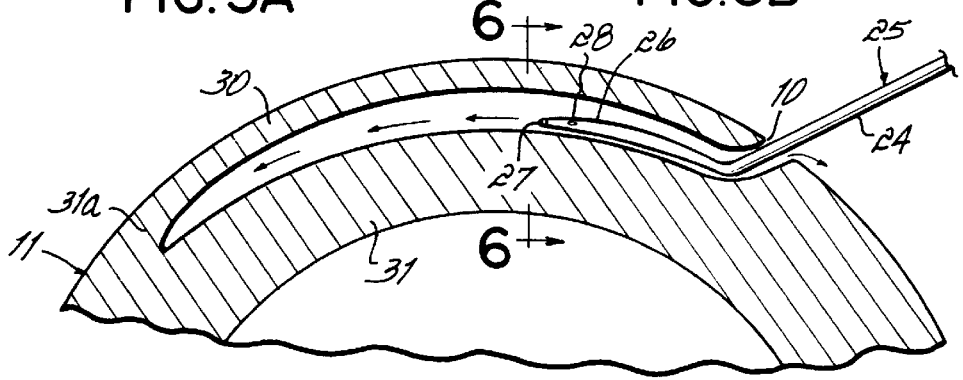

FIG. 4 illustrates a side view of an irrigation cannula for use with the method of the present invention engaging the interface of the corneal flap and stromal bed with an angled stem.

Figure 5:
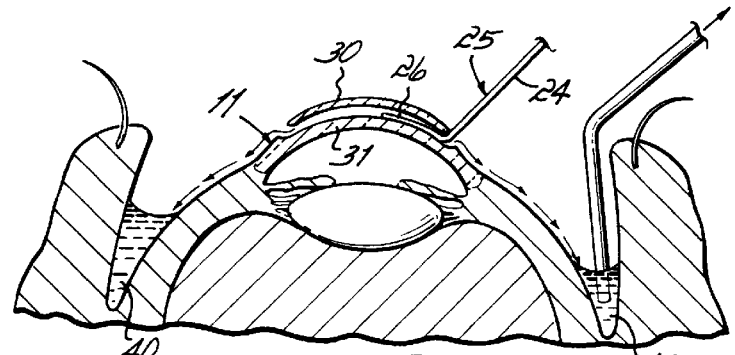

FIG. 5 illustrates a side view of a cannula and irrigation technique of the method of the present invention wherein an irrigation cannula engages the corneal interface and gently lifts the corneal cap from the stromal bed while an aspirating cannula removes the residual fluid and debris that has collected in the fornices after being removed from the corneal interface.

Figures 6, 8:
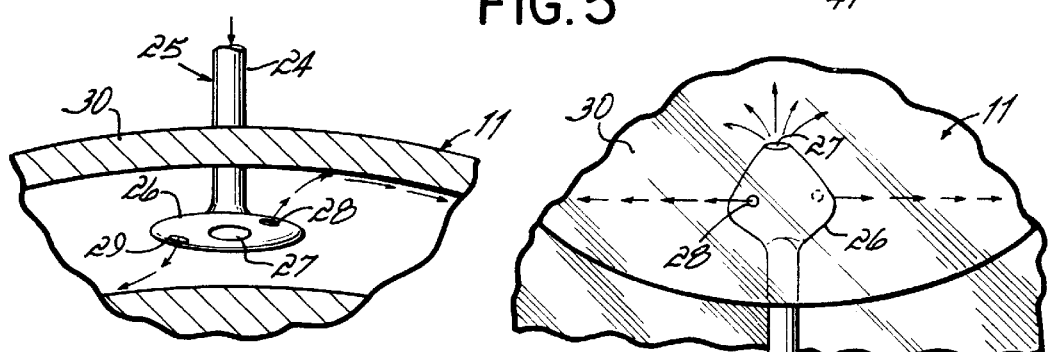

FIG. 6 is a cross-sectional view taken in lines 6—6 of FIG. 5 of the cannula for use with the method of the present invention wherein the desired low flow pattern emanating from the angled ports of the cannula gently lifts the corneal flap or cap from the stromal bed and moves debris and particulate to the periphery.

Figure 7:
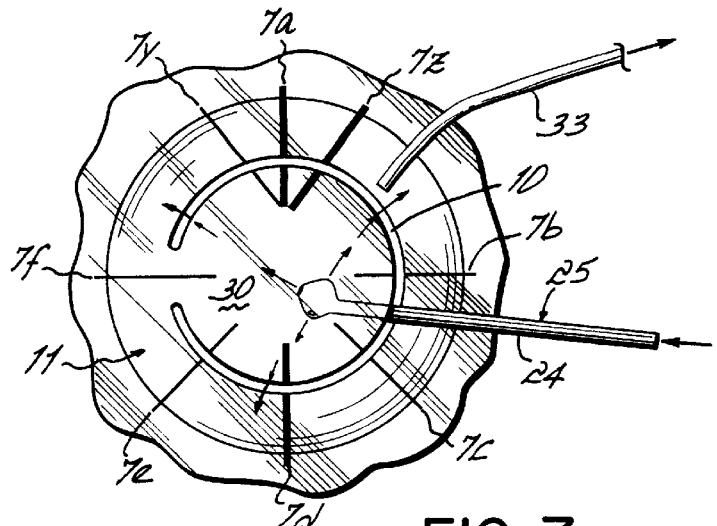

FIG. 7 illustrates a top view of a cannula and the irrigation technique of the method of the present invention eliminating epithelium and debris from the corneal interface and aspirating the residual fluid and debris from the edge of the keratectomy. Also illustrated are preoperative markings on the corneal surface for anatomically aligning the corneal flap or cap correctly.

FIG. 8 illustrates an enlarged top view of a cannula for use with the method of the present invention wherein the flow pattern emanating from a flat tip and angled side ports of the cannula end is demonstrated.

Figure 9:
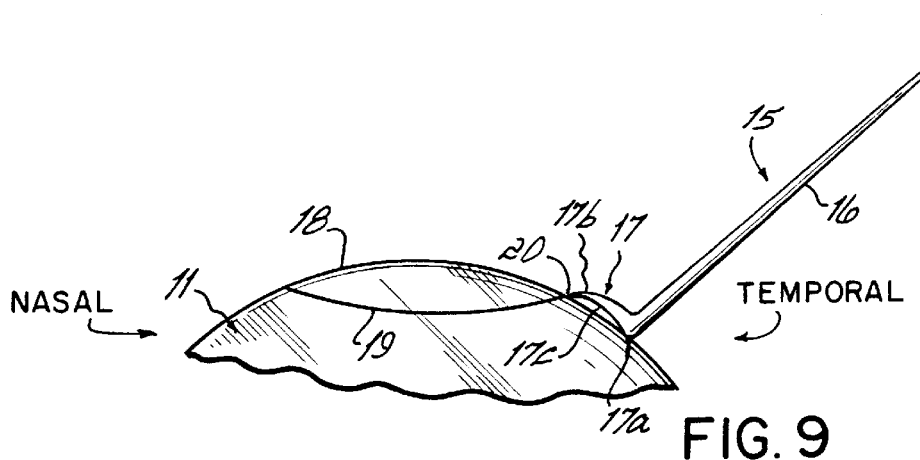

FIG. 9 illustrates a side view of the corneal flap or cap elevating instrument for use with the method of this invention. The instrument has a handle and a vertically curved bottom portion that engages the corneal surface and keratectomy edge.

Figure 10:
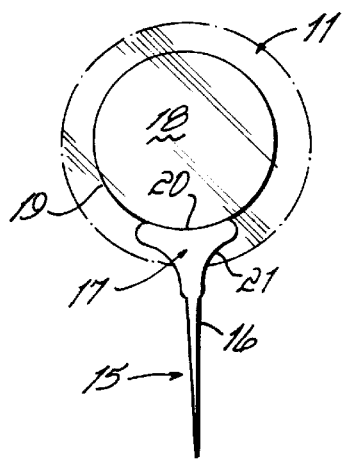

FIG. 10 illustrates a top view of the elevating instrument for use with the method of this invention engaging a keratectomy edge on the corneal surface prior to lifting a corneal flap or cap.

Figure 11:
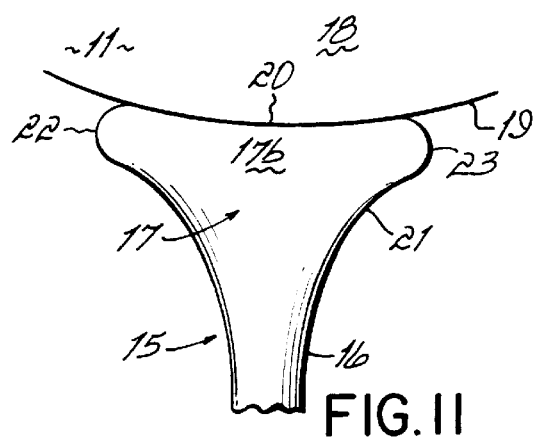

FIG. 11 illustrates an enlarged view of the region of FIG. 10 where the bottom portion of the elevating instrument engages and conforms to the keratectomy edge of the corneal surface.

DETAILED DESCRIPTION OF THE INVENTION

The present invention and its advantages will be better understood from the following outlined stages of the surgical procedure for repositioning a lamellar corneal flap/cap to reduce irregular astigmatism and debris/epithelium in the interface during low flow tectonic lamellar surgery. The detailed description incorporates references to the accompanying figures. In the various figures, like reference characters are used to designate like parts.

OVERVIEW OF THE SURGICAL PROCEDURE

Figure 1:
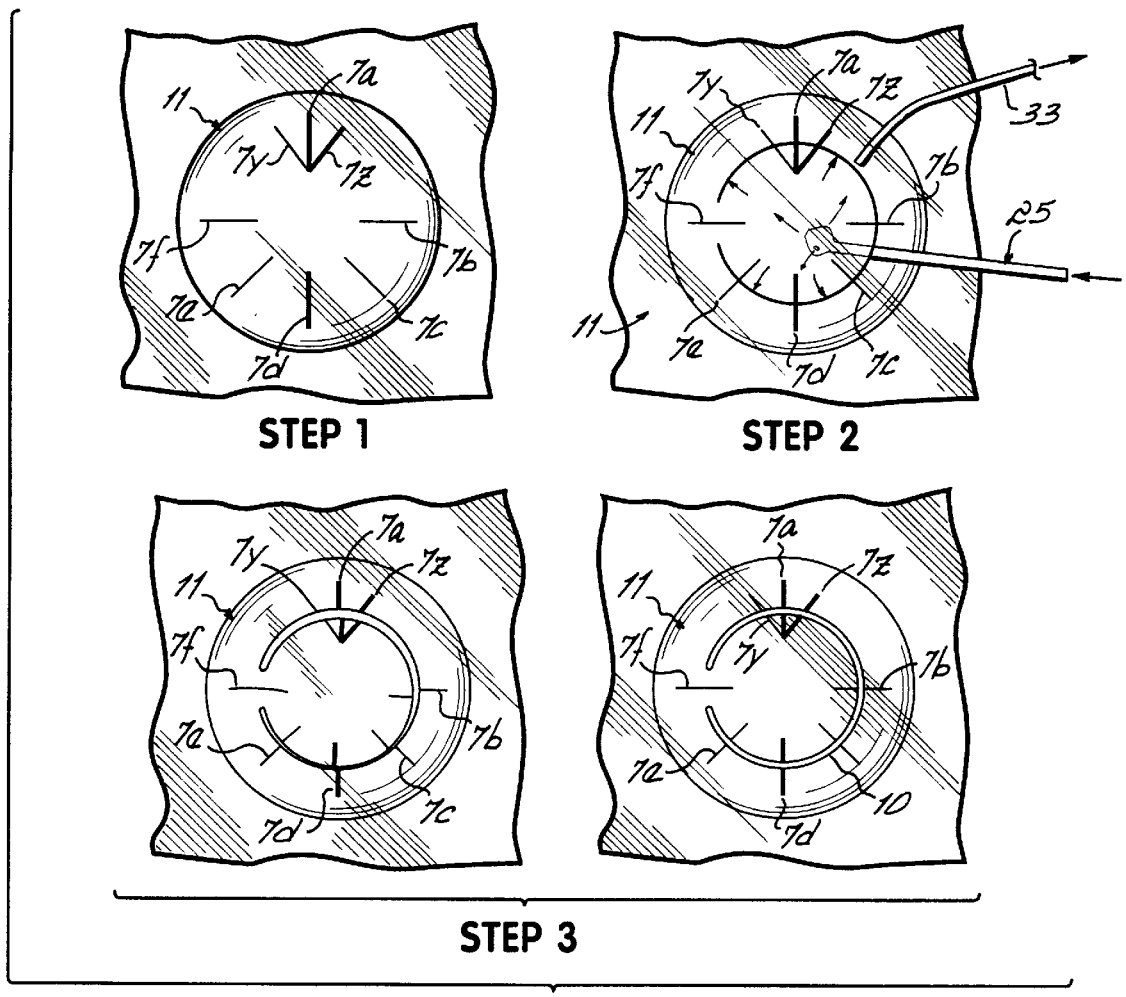
FIG. 1 illustrates sequentially the steps of the method of the present invention. Step 1 provides for preoperatively marking the corneal surface with a corneal surface marker having the indicated reference marks. Step 2 provides for removing epithelium and debris after surgical reshaping of the corneal stroma through irrigation and aspiration. Step 3 provides for aligning the corneal cap or flap to its correct anatomical position with forceps or suitable instrumentation using the preoperative markings.

As shown in FIG. 1, prior to a lamellar dissection, a marker is used to outline in a specific configuration the present anatomical surface of the cornea (See Step 1). Once the lamellar dissection is made, the surgical reshaping accomplished and it is appropriate to return the corneal cap/flap to its correct anatomical position, the corneal bed is irrigated with low flow. As seen in the top view of Step 2, fluid is aspirated from the fornices such that fluid flows from the bed (top of the dome of the eye) out and downward to the fornices. This second step removes debris and epithelium from the interface. Irrigation should start centrally in the stromal bed and move peripherally toward the keratectomy. The second step also requires the suction cannula to be placed gently on the edge of the keratectomy to prevent debris/epithelium from wicking back under the flap/cap.

Lastly, with a layer of irrigation fluid in the interface, the corneal flap/cap is then aligned with the preoperative surface marking (See Step 3). If debris continues to be present or the cap is not aligned, the method is repeated.

A. Preoperative ALK or LASIK

1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS should be conducted. As many have noticed for a long time during cataract surgery when meibomian secretions present as a layer in a pool of irrigating solution, a quick irrigation with the I&A with the head tilted will remove this oily film in a large sheet. This is what we believe is happening when they tilt the patient's head and have already done the lid scrubs and irrigate the fornices. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative

1. Draping

This is one of the most important steps. Whatever drape you plan to use, it must retract the eyelashes out of the field and the drape should not restrict the speculum from opening fully so that adequate exposure of the globe can be obtained for suction. We presently use a 10–24 drape made by 3M to accomplish this.

2. Irrigation System

At present, we have been using the roller clamp on the IV bottle to control the flow of the BSS Plus through the irrigation cannula. We have found that it is best if this flow is just adequate to float a cap or flap off the bed without creating distortions, undulations or undue turbulence. This irrigation can also be used to irrigate the globe and cornea prior to surgery.

3. LASIK Corneal Marker and Marking Method

The most recent advancement in corneal surgery is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication of LASIK corneal surgery which can be sight threatening is irregular astigmatism. To date, corneal surgeons have used subtle and often imperceptible visual cues to reapproximate the flap or corneal tissue. It is apparent that a slight decentration or disorientation of the flap can result in irregular astigmatism.

Thus, with the above preoperative surgical procedures detailed and the dramatic problems of imprecise results of corneal surgery outlined, we propose an embodiment of a corneal surface marker of the present invention shown generally at 5 in FIGS. 2A and 2B of the drawings. The corneal surface marker 5 improves centration of the surgical procedure and apparatus and precisely repositions the corneal cap or flap after the ablation stage of the surgical procedure.

In its most preferred embodiment, the Kritzinger-Updegraff (KU) LASIK marker 5 of FIG. 2 consists of a handle 6 and two concentric rings, 7 and 8; ring 7 being 5 mm in diameter d, with crosshair 9 (to aid centering) and ring 8 being 10 mm to 10.5 mm in diameter $d_2$. The rings 7 and 8 of FIG. 2 may be formed of metal with radial blades 7a–7f and 7y–7z pararadial blades extending therefrom as shown by FIG. 2b in cross-sectional view along blades 7f and 7b. The blades may be used to deliver dye to the corneal surface as the marking indicia. The diameters of the rings are important in that they approximate the specific areas of the cornea to be covered and eventually worked. Further, radiating off the center ring 7 are six radials, shown in the figures as 7a, 7b, 7c, 7d, 7e, 7f, and two pararadials, shown as 7y and 7z, which extend approximately 6 mm from the center of the crosshair or at any length $d_3$ sufficient to cross and give adequate reference points past ring 8. These radial and pararadial markers vary in width as shown in FIGS. 2 and 3 which permits precise repositioning of the cap or flap edges after the keratectomy and ablation have been performed. Further, as shown in FIG. 1, step 1, when marker 5 is properly placed over the eye in the position indicated and, where the OD of the cornea 11 is outlined, the pararadial and radial marks are made by a dye using elements 7a–7f and 7y–7z. These surrounding regions are the nasal, temporal, inferior and superior. The width of the superior radial 7d and inferior radial 7a as well as the temporal pararadial 7z are at least two times thicker than the other radials 7b, 7c, 7e, 7f and pararadial 7y. The pararadials 7y and 7z at 11:00 and 1:00 are of different width to ensure proper orientation of a free cap and prevent placement of a free cap upside down (epithelial surface down). The marker 5 was developed to permit a centered keratectomy which is dependent upon outer ring 8 on which the surgeon centers a suction ring before the surgical incision is made. Additionally, the concentric rings 7 and 8 ensure centration of the mark and subsequent centration of the LASIK suction ring or other appropriate instrumentation during the course of the surgical steps. The different widths of the pararadials and radials permit accurate, anatomic repositioning of the cap or flap after ablation microsurgery of the cornea is complete. The radial and pararadial markings also provide adequate reference points with the large flaps made with the LASIK suction ring.

As shown in FIGS. 2a–2b, the radiating markers 7a–7f and 7y–7z extend beyond the ring created by the keratectomy also prevents micro-decentration seen when the surgeon uses an equally gapped gutter 10 in the cornea 11 as the cue for alignment. This imprecise method of alignment is thus rendered unnecessary.

When the marker 5 described in detail above is properly placed in position over the corneal surface as illustrated in FIG. 1, step 1, and the marking radials and pararadials are aligned correctly, suitable pharmacologically safe dyes are preoperatively placed as indicia on the corneal surface in the pattern outlined by the marker 5 so that the keratectomy and stromal reshaping by the surgeon may begin. Thereafter, the radial and pararadial markings are then aligned so that the free corneal cap or flap is accurately, anatomically positioned thereby reducing the possibility of astigmatism post surgical procedure. The correct anatomical alignment is illustrated in FIG. 3b of the drawings.

4. Centration a. Positioning the Patient's Head

The goal is to have the globe absolutely centered in the patient's socket as the patient fixates on the red fixation beam. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the cross-hairs that are in the optics of the right eye piece. The KU marker is then positioned so that the superior and medial lateral marks of the cross-hair match with those of the marker. Thus, after creating the mark the cross-hairs can be superimposed upon it. If there is not absolute correspondence of the cross-hairs in the mark that is placed on the cornea, the surgeon is then responsible to make a "mental note" of this orientation when ablating the stromal bed and putting the flap back into position. At this point with the Keracor 116 laser, the red and green light must be superimposed prior to placing these marks or the cross-hair will move away from the center of the pupil after these maneuvers have been performed.

b. Applying the Suction Ring

It is important to have the circular mark of the KU marker aligned concentrically with the suction ring. This ensures that the flap will be central to the pupil.

c. Ablation

After the keratectomy is performed, the flap is folded back nasally. The peripheral markings of the KU marker are still visible. Thus, these are used as a visual cue to line up the cross-hair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient's head has moved and thus must be oriented back to the position you had initially worked so hard to achieve. Do not play with the joy stick.

d. Added Security Measures

When using the Keracor 116 laser, leave all three lights on; two red lights and one green light. The one red light with a green indicates that as you are lasering you are at the correct level of focus. The other red light follows the actual laser and indicates the orientation of the laser beam whether it is astigmatism or spherical correction. This is an added security measure to ensure that you are lasering the proper axis.

e. Centering Pearl

When you are lasering, turn the light down and ask the patient continuously to look into the red fixation light. This is a cross-check to ensure that the patient is centering on the cross-hair and that the laser treatment is in the center of the pupil. Between each zone of treatment, we recommend either using a spatula or hockey stick to wipe excess fluid from the stromal surface.

f. Addendum to Centration

Eye trackers can be very helpful, however, we feel that these steps in centering the globe are much more fail-safe and ultimately efficient.

5. Suction Rings a. Adjustable Ring

The adjustable suction ring can be used for LASIK, however, this consistently creates a small flap or cap. On average, the diameter is 7.2 mm. For standard ALK cases, we do not recommend routinely trying to use the excimer laser suction ring because the grooves in the sclera that this creates do not match the adjustable suction ring and it can be difficult to center your suction ring for the very critical refractive pass with standard ALK.

b. LASIK Suction Ring

This ring has a larger inside diameter than the adjustable suction ring and it allows the keratome to be exposed to more cornea thus creating keratectomies which are on the average 8.55 mm in diameter. This is the suction ring of choice for LASIK. However, when placing this suction ring on a globe that retropulses fairly freely, it is important to proptose the globe with a speculum so that the suction ring has a firm adherence to the globe prior to initiating suction. Because the outside of the LASIK suction ring is a smaller diameter than the adjustable suction ring, firm pressure on the suction ring handle can retropulse the globe and thus make it difficult to have clearance for the keratome. The adjustable suction ring on the other hand has a large place that will rest on the eyelids and if the globe is proptosed it will be held by the suction of the suction ring and in turn the suction plate will be held upwards by the lid thugs providing easier exposure. This will become less of significance as surgeons gain experience with the fixed LASIK suction ring.

6. Ablation

Remember to center with KU marker cues.

7. Irrigation Cannula and Method for Low Flow Keratoplasty a. Irrigation Cannula and Technique With the most recent advancement of excimer laser in situ keratomileusis and its popularization, it has become necessary to develop instruments which will reduce the most significant complications of lamellar surgery: irregular astigmatism and debris/epithelium in the interface. We described above a method and instrument for marking, aligning and returning the overlying corneal flap to its correct anatomical position. We now describe in detail an irrigating cannula and technique that will remove debris from the interface and improve on the problem of postoperative irregular astigmatism stemming from lamellar keratoplasty.

With reference to FIGS. 1 and 4–8, once the keratectomy is made, an anterior chamber irrigating cannula 25 of the present invention is introduced underneath the flap and into the interface between corneal flap or cap 30 and bed 31. Cannula 25 has an angled stem or handle 24 which enables the introduction into the interface.

As previously mentioned briefly and as shown in FIGS. 4 and 5, the irrigation flow should be adjusted so that the cap/flap 30 floats gently above the bed 31. The goal is to have the patient fixating so that the apex of the globe is in line with the microscope. This allows the fluid to flow from underneath the cap or flap 30 peripherally and out past the limbus into the fornices 40 and 41. The fornices can be aspirated with a low flow aspirating suction cannula 33 (see FIG. 5). This removes epithelial debris and lint from the interface. After approximately 15 to 20 seconds of this form of irrigation, the irrigating cannula 25 can be moved centrally towards the stromal hinge 31a and gently swept back and forth from the hinge 31a and then held centrally again (see FIG. 8). This allows any epithelium entrapped by the blade at the hinge 31a to be freed and irrigated out. Once the fornices 40 and 41 are cleared of fluid, the aspiration cannula 33 can be moved towards the gutter 10 and with a low flow irrigation, the cap 30 can be nudged so that the radial and pararadial preoperative marks are fairly aligned. Once this is achieved, the gutter 10 should be aspirated 270 degrees while there is steady irrigation (see FIGS. 5 and 7). This again removes debris that could have hung up at the edge of the keratectomy and not run to the fornices 40 and 41. Aspiration of the gutter 10 is continued as the irrigating cannula is gently withdrawn taking note of the approximation of the radial and pararadial marks.

We are presently using a curved tying forceps to smooth the flap or cap 30 from the center to the periphery in making sure the radial and pararadial marks are aligned. If alignment is not achieved, the irrigating cannula 25 is once again reintroduced and aspiration is performed in the gutter 10 while the cap 30 is allowed to be adjusted on a bed of fluid.

Referring particularly to FIGS. 4–8 of the drawings, the cannula shown generally at 25 between corneal flap or cap 30 and the stromal bed 31 has three 25 gauge irrigating ports on its end 26. One of these ports, 27, located at the tip of end 26 will deliver low flow irrigating fluid directly from the tip. The other two ports will be approximately 90 degrees away with one, 28, elevated and angled superiorly and one, 29, angled inferiorly. As illustrated in FIGS. 6–8, on low flow with balanced salt solution, the irrigating cannula 25 with its unique port configuration generates a flow pattern indicated by arrows that very gently elevates and suspends the overlying corneal flap or cap 30 while washing debris and epithelium to the inferior fornix where it is aspirated with a suction cannula. The constant irrigation of the bed 31 which is at the apex of the dome of the cornea and globe will allow debris to be removed from the interface preventing postoperative irregular astigmatism.

Referring to FIGS. 5 and 7, the final maneuver is to aspirate with suction cannula 33 residual fluid from the gutter 10 out of the keratectomy to ensure that no particles will be wicked back into the interface once the fluid has decreased. This is done while the irrigating cannula 25 is delivering low flow fluid from the center of the interface to the periphery (towards the keratectomy).

By utilizing the preoperative markings 7a through 7f and 7y and 7z from the above described Kritzinger/Updegraff LASIK marker and marking method, the cornea is gently massaged with a blunt forceps or a moistened sponge so the cornea is returned into the correct anatomical position. If any wrinkling of the corneal cap or flap is evident or there is not correct alignment of any of the eight (8) radial or pararadial marks, then the irrigating cannula is reintroduced and the cap or flap repositioning procedure is performed again.

In its most preferred form, the irrigating cannula 25 at FIG. 8 is approximately 25 gauge in diameter and most notably has a flat triangulated end 26, the tip of which is blunt. The blunt tip has a port 27, a port 28 coming out from the top of the left sided portion of end 26, and a port 29 (shown in FIG. 6) emanating fluid from the bottom or the right sided portion of the triangulated end 26. This allows flow of fluid not only directly away from the cannula out of port 27, but also up and out from port 28 and down and out from port 29. This flow pattern from the cannula 25 allows a gentle flow of fluid between the corneal cap or flap 30 and the lamellar bed (shown in FIG. 5) elevating the cap while cleansing the corneal bed of debris and loose epithelium.

b. Cap/Flap Adherence (1) Use of Air on Corneal Surface.

Air blown on the surface of the cornea can be used working from the center of the corneal surface to the periphery for adherence to the cap/flap. This wicks out fluid from the center to the gutter which again improves the removal of debris and epithelial inclusions from the interface. We believe that there is a higher incidence of folds or cracks in Bowman's membrane when air is used. We also believe that using surface air requires one to work very quickly, because the cap will adhere very rapidly, thus it must be well-centered before the air is introduced. Presently, we prefer to use merocel sponges and very carefully use the tip of this to wick the fluid from the gutter and out from underneath the cap/flap. Extreme care must be taken when using the merocel to remove the fluid in that the patient must have solid fixation. If the patient looks into the wech-cel, the edge of the cap or flap will become bunched up and potentially dislodge the perfect orientation we had previously achieved with the irrigation and aspiration maneuver. However, we do find that with approximately three minutes of time the cap or flap is quite adherent by using this maneuver.

(2) Adherence Tests (a) Slade Stria Test

By taking a pair of curved tying forceps and gently depressing approximately 1–2 mm away from the keratectomy gutter, one can see folds or stria originating from the point of depression in the cornea up past the gutter and on the surface of the cap or flap. This should be seen for 360 degrees upon depression. If there are no stria two things are occurring, i) the cap of flap has not adhered to the bed; ii) the cap of flap has possibly folded on itself on the edge and is preventing adherence of the or flap. With the merocel drying technique, We typically place a drop of BSS on the central cornea while drying the gutter. This improves postoperative visual recovery and aids in patient fixation.

(b) Blink Test

Have the patient repeatedly blink his or her eyes following the Slade Stria Test to confirm the adherence of the cap or flap. One must be very cautious when removing the 10–24 drape. We typically remove the drape as we remove the lid speculum and that way the lid speculum retracts the drape away from the globe as we move them simultaneously. Caps and flaps have been dislodged upon removing speculums and more likely when the edge of a sharp drape catches the keratectomy of the cap and either totally dislodges it or disorients it so that irregular astigmatism is present after surgery. On should always check with the blink test after the drape is removed.

8. Corneal Flap or Cap Elevator

With recent advancement and popularity of LASIK which is outlined in detail above, there has been a growing need to provide a system for accurate retreatment of these patients. Due to the varied ability and surgeon variation in ablation patterns, under corrections of the patient's refractive error can result. Some surgeons have advocated performing a complete new lamellar keratectomy. However, this has been shown to cause slivering of the cornea and sometimes resulting in irregular astigmatism or loss of best corrected visual acuity.

We propose lifting the corneal flap or cap when it is less than five months after the initial surgery and repositioning of the corneal cap. We have developed a corneal elevating instrument to atraumatically lift the edge of the flap or cap prior to using the above described Kritzinger/Updegraff LASIK corneal surface marker and irrigating cannula. This corneal elevator will be used to expose the corneal edge and a Colibri forceps can be used to peel back the overlying cap or flap. After the desired ablation is obtained, the flow tectonic repositioning of the corneal cap as described above is then used to return it to its correct anatomic position.

With particular reference to the accompanying drawing FIGS. 9, 10 and 11, the corneal cap or flap elevating instrument of the present invention is shown generally at 15.

More particularly, FIG. 9 illustrates a side view of the elevating instrument 15 for use in atraumatically lifting a corneal cap or flap during corneal lamellar surgery. The instrument 15 has a stem or handle 16 which is angularly disposed, i.e., about 90°, with respect to the elevator head 17 to facilitate lifting in a preferred manner. The elevator head 17 is a curved blade having a vertical curvature whereby only the heel 17a and toe 17b engage the corneal epithelial surface 18. Further, toe 17b of instrument 15 engages the edge 19 of the keratectomy incision that was made by the surgeon and forces the edge 19 upward exposing the underlying surface for corrective ablation. Thus, the elevator head 17 has an incline convex top face extending vertically away from a concave arcuate edge 20 which conforms to the edge 19 of the keratectomy. The heel 17a and toe 17b sections of head 17 have a bottom surface 17c which is concave in the preferred form so that only the heel and toe sections engage the corneal surface atraumatically.

Referring particularly to FIG. 10 which illustrates a top view of the present invention, instrument 15 engages the keratectomy edge 19 with elevator head 17. Keratectomy edge 19 circumferentially outlines a corneal flap or cap which is approximately 7 mm to 8 mm in diameter. The arcuate convex edge 20 atraumatically engages corneal keratectomy edge 19 where an initial incision has been made by the surgeon and atraumatically lifts corneal edge 19 to expose the underlying surface to be surgically altered or reshaped.

FIG. 11 illustrates an enlarged section of FIG. 10, and shows the arcuate edge 20 having a blunt or dull beveled portion 21. The beveled portion 21 aids in atraumatically lifting the corneal edge to expose the underlying surface. The edge 20 has rounded ends 22 and 23. These prevent the tearing or other unintentional destruction of the corneal cap or flap when the edge 19 is engaged and lifted in order for the cap to be grasped and peeled by Colibri forceps prior to corrective ablation. In a preferred form, the dull and beveled portion 21 of arcuate edge 20 is gradually sloped to conform to keratectomy edge 19 and is approximately 3 mm to 4 mm in length. Thus, the elevator 17 can be gently swept across the corneal surface and will help the surgeon engage at the edge of where the initial incision was made temporally. The gentle sweeping will facilitate the lifting of the corneal flap or cap without tearing or causing distortion.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

We claim:

1. A method for reducing irregular astigmatism and debris during lamellar surgery of the eye for repositioning an excised corneal cap or flap onto a corneal bed comprising preoperatively marking a corneal surface with suitable indicia thereby providing adequate reference marks on said surface for incision and precise centration and reorientation of said cap or flap onto a corneal bed after surgical reshaping of the corneal stroma, incising said corneal surface to form said cap or flap, reshaping the corneal stroma, removing debris from the interface of said corneal bed and cap or flap by irrigating said corneal bed with low flow fluid ejected from a cannula, aspirating fluid and debris from the eye, and aligning to a correct anatomical position said cap or flap utilizing said preoperative surface indicia.

2. The method according to claim 1 further comprising preoperatively marking the corneal surface with dye in a pattern of radial and pararadial lines extending over the area of the cornea through which said incision will be made to excise said cap or flap, at least one radial line and at least one pararadial line converging upon each other at an angle within said area, circumferentially incising said corneal surface across said radial and pararadial lines to form said cap or flap, removing said cap or flap from said surface having said radial and pararadial lines partially remaining both on the cap or flap and the remaining corneal surface for postoperative realignment, and realigning said partially remaining radial and pararadial lines of said cap or flap with those on the remaining corneal surface.

3. The method according to claim 1 further comprising placing a corneal surface marker over the area of the cornea to be marked, said marker having two concentric rings ensuring centration of said marker, a marking radial and pararadial extending off said rings thereby providing adequate reference points for the marking indicia to be placed on the corneal surface, said radial and pararadial varying in width, said step of preoperatively marking the corneal surface conducted with suitable indicia in accordance with the radial and pararadial of said marker.

4. The method according to claim 3 wherein said inner and outer concentric rings of said marker are circumferentially sized to outline the cornea surface and the optical zone of said corneal surface ensuring accurate centration of said marker.

5. The method according to claim 3 wherein said suitable indicia used for marking is a pharmacologically safe dye.

6. A method according to claim 3 by marking with radials and pararadials of varying width and extending beyond the outer concentric ring.

7. A method of marking the corneal surface according to claim 3 by marking with said concentric rings of approximately 5 mm and 10 mm, respectively.

8. A method according to claim 3 by marking radials and pararadials sufficiently circumferentially spaced around said concentric rings to provide said adequate reference marks.

9. A method according to claim 3 by marking with two pararadials extending off the inner concentric ring from a common point at a 90° angle with respect to each other.

10. A method according to claim 3 by marking two pararadials of unequal width, one pararadial being at least about twice as wide as the other pararadial.

11. The method according to claim 1 further comprising irrigating by inserting a corneal irrigating cannula having a plurality of irrigating ports into said interface of said cap or flap and bed, delivering said fluid under low flow through said plurality of irrigating ports and irrigating said interface by gently elevating said cap or flap and washing residual debris and epithelium from said corneal bed.

12. The method according to claim 11 by delivering said fluid from about the center of said corneal bed and moving said fluid peripherally toward the edge of said bed and cap or flap.

13. The method according to claim 11 wherein said corneal irrigating cannula is a hand manipulatable tube and irrigating said corneal incision by hand.

14. The method according to claim 11 by irrigating with three separate streams of fluid directed to said interface by said ports.

15. The method according to claim 14 wherein one of said fluid streams is delivered directly outward from an end of said cannula.

16. The method according to claim 14 with at least two of said streams directing fluid upward and downward thereby elevating said overlying cap or flap and washing residual debris and epithelium from said corneal bed.

17. The method according to claim 16 by separately directing said two streams approximately 180 degrees from one another.

18. The method according to claim 17 by directing an additional stream in a direction approximately 90 degrees from the direction of each of said two streams.

19. The method according to claim 11 wherein said fluid is a pharmacologically safe solution.

20. The method according to claim 11 wherein said irrigating ports are each approximately 25 gauge in diameter.

21. The method according to claim 1 further comprising providing a cornea elevating instrument having an elevator head with a leading edge and an inclined top face extending vertically away from said edge, placing said instrument at the edge of the corneal cap or flap incision, exposing said corneal flap or cap edge by inserting the elevator edge into the incision and atraumatically lifting said edge on said inclined top face, and peeling back said edge to provide said cap or flap before reshaping the corneal stroma.

22. The method according to claim 21 by placing said elevating instrument at the incision edge for lifting said corneal flap or cap in the temporal region of the corneal surface.

23. The method according to claim 21 wherein a forceps is used for peeling back said corneal flap or cap.

24. The method according to claim 21 wherein said elevating instrument has an elevator head with a convex inclined top face and a concave leading edge, placing said instrument at the edge of a circumferential corneal cap or flap incision for atraumatically lifting the flap or cap.

25. A method for reducing irregular astigmatism and debris during lamellar surgery of an eye for repositioning an excised corneal cap or flap onto a corneal bed comprising preoperatively marking a corneal surface with a pattern of radial and pararadial lines extending over the area of a cornea through which an incision will be made to incise a cap or flap, circumferentially incising said corneal surface across said radial and pararadial lines to form said cap or flap, removing said cap or flap from said surface having said radial and pararadial lines partially remaining both on the cap or flap and a remaining corneal surface for postoperative realignment, reshaping a stroma of the cornea, removing debris from an interface of said corneal bed and cap or flap by irrigating said corneal bed with low flow fluid ejected from a cannula, said cannula having a plurality of irrigating ports for delivery of fluid by gently elevating said cap or flap and washing residual debris from the corneal bed, aspirating fluid and debris from the eye, and realigning said partially remaining radial and pararadial lines of said cap or flap with those on the remaining corneal surface.

26. The method according to claim 25 by marking with radials and pararadials of varying width.

27. The method according to claim 26 by marking with two pararadials extending from a common point at an angle with respect to each other.

28. The method according to claim 26 by marking two pararadials of unequal width.

29. The method according to claim 25 by irrigating said corneal bed with a plurality of streams for directing fluid upward and downward thereby elevating said overlying cap or flap and washing debris from said corneal bed.

30. The method according to claim 25 by further providing a corneal elevating instrument having an elevator head with a leading edge and an inclined top face extending vertically away from said edge, placing said instrument at the edge of the corneal cap or flap incision, exposing said corneal flap or cap edge by inserting the elevator edge into the incision and atraumatically lifting said edge on said inclined top face, and peeling back said edge to provide said cap or flap before reshaping the corneal stroma.

* * * * *